United States Patent
Suplie et al.

(10) Patent No.: US 9,943,488 B2
(45) Date of Patent: *Apr. 17, 2018

(54) GAMMA HYDROXYBUTYRIC ACID GRANULES

(75) Inventors: Pascal Suplie, Montaure (FR); Sylvie Lecoustey, Mezieres en Drouais (FR)

(73) Assignee: DEBREGEAS ET ASSOCIES PHARMA, Paris (FR)

( * ) Notice: Subject to any disclaimer, the term of this patent is extended or adjusted under 35 U.S.C. 154(b) by 888 days.

This patent is subject to a terminal disclaimer.

(21) Appl. No.: 13/984,922

(22) PCT Filed: Feb. 3, 2012

(86) PCT No.: PCT/FR2012/000046
§ 371 (c)(1),
(2), (4) Date: Sep. 11, 2013

(87) PCT Pub. No.: WO2012/107652
PCT Pub. Date: Aug. 16, 2012

(65) Prior Publication Data
US 2014/0004202 A1    Jan. 2, 2014

(30) Foreign Application Priority Data
Feb. 11, 2011   (FR) ..................... 11 00433

(51) Int. Cl.
*A61K 9/16* (2006.01)
*A61K 9/50* (2006.01)
*A61K 9/46* (2006.01)
*A61K 9/00* (2006.01)
*A61K 31/19* (2006.01)

(52) U.S. Cl.
CPC .............. *A61K 9/50* (2013.01); *A61K 9/0007* (2013.01); *A61K 9/0065* (2013.01); *A61K 9/501* (2013.01); *A61K 9/5078* (2013.01); *A61K 9/5084* (2013.01); *A61K 31/19* (2013.01)

(58) Field of Classification Search
CPC ...... A61K 9/50; A61K 9/0007; A61K 9/0065; A61K 9/501; A61K 9/5078; A61K 9/5084; A61K 31/19
USPC .......................................... 424/490
See application file for complete search history.

(56) References Cited

U.S. PATENT DOCUMENTS

2006/0210630 A1    9/2006    Liang et al.
2011/0293729 A1*  12/2011   Lebon .................. A61K 9/1611
                                                              424/494

FOREIGN PATENT DOCUMENTS

| EP | 1 273 301 A2 | 7/2002 |
| WO | WO 2010/055260 A1 | 5/2010 |
| WO | WO 2010/055268 A1 | 5/2010 |
| WO | WO 2011/018583 A2 | 2/2011 |

OTHER PUBLICATIONS

"Rohypnol," *Connecticut Clearinghouse—A Program of Wheeler Clinic*, pp. 1-2, Jan. 1, 2003.
International Search Report issued in Application No. PCT/FR2012/000046; dated Apr. 27, 2012 (With Translation).

* cited by examiner

*Primary Examiner* — Adam C Milligan
(74) *Attorney, Agent, or Firm* — Benjamin S. Prebyl

(57) ABSTRACT

A granule including a solid core on which is supported an active ingredient, said active ingredient being selected from gamma-hydroxybutric acid or one of its pharmaceutically acceptable salts, said granule further including, supported on said solid core, one or more compounds which may generate gas evolvement, one or more diluents, said granule being in that it is coated with a membrane, and in that the solid core represents from 15% to 50% by weight based on the total weight of the granule.

10 Claims, 14 Drawing Sheets

GAMMA HYDROXYBUTYRIC ACID GRANULES

The object of the present invention is gamma-hydroxybutyric granules, as well as pharmaceutical positions containing them. Gamma-hydroxybutyric acid (GHB or sodium oxybate) is a natural metabolite present at the level of the brains of mammals; its chemical structure is close to gamma-aminobutyric acid (GABA), a neurotransmitter, whence its activity on the central nervous system.

This active ingredient was used as a general anesthetic and as a hypnotic in the treatment of insomnia. Presently it is especially used in certain sleep disorders, such as cataleptic in narcoleptic patients, under the commercial name of Xyrem®, in an amount of two night takings of solute. Within this scope, the patient takes an initial dose at bedtime and has to get up at about four hours later for a second night taking.

GHB is highly soluble, hygroscopic and strongly alkaline. The therapeutic doses are very high. Indeed, in the treatment of narcolepsy, the doses used range from 4.5 to 9 g of active ingredient per day.

Moreover, GHB is frequently used a recreational drug with different goals: deinhibition, relaxation, search for physical or sexual performances.

The whole of these characteristics show the benefit of having a prolonged release form of this active ingredient. Many studies were conducted in this direction. Thus, different oral prolonged release formulations may be reported in the prior art without however any of them providing a complete answer to the whole of this complex problem.

U.S. Pat. No. 5,594,030 describes pharmaceutical compositions appearing as granules or tablets containing GHB in a cellulose matrix; these pharmaceutical preparations exhibit dissolution over a period from 7 to 8 hours.

EP 0 635 265 describes controlled release pharmaceutical compositions based on a salt of gamma-hydroxybutyric acid consisting of a core, in the form of granules or tablets, comprising the active ingredient dispersed in a cellulose matrix. A controlled release form is thereby obtained by diffusion through membranes aiming at a release of the active ingredient in the upper portion of the digestive tract.

Application US2006/210630 describes pharmaceutical compositions with controlled release of GHB consisting of particles comprising the active ingredient as a core. These particles are then covered with a protective layer, the latter being itself covered with a second layer for enteric release.

Immediate or gastro-protective particles are therefore known from the state of the art, which may be used alone or as a combination.

Application PCT WO 2010/055260 describes a granule comprising a solid core on which GHB is supported, optionally calcium carbonate, PVP, a coloring agent, said granule being coated with a layer of hypromellose and then of hypromellose phthalate.

The granule described in this application allows reduction in the daily dose and the number of daily takings, by increasing the apparent half life and bio-availability of the active ingredient. Moreover, it is provided with means which reduce misuses.

Finally, this is actually an essential point, the solid core of said granule represents 11.48% by weight based on the total weight of the granule.

It is important to recall that the problem of GHB is complex and multiple: indeed, GHB is extremely soluble and after oral administration, absolute bio-availability is only 25%. Average times for attaining plasma levels range from 30 minutes to 2 hours, absorption being very variable from one individual to another.

Elimination is essentially accomplished by metabolization into carbon dioxide with a half life ranging from 30 minutes to one hour. However the absorption seems to be of limited and region-specific capacity and more particularly located at a very high level in the digestive tract (Palatini et al, European Journal of Clinical Pharmacology, 1993).

The whole of the formulations described in the prior art mention prolonged release forms and more particular gastroprotective forms, i.e. for which the release of GHB will occur upon exiting the stomach, this by means of the use of a pH-dependent polymer (dissolution of the polymer at a pH of 5.5 or 6).

In this case and also in the case of matrices, a shift is physiologically obtained in the absorption time of GHB. This is however not completely satisfactory since the dwelling time at the preferential absorption sites remains limited and more the effect of prolonged release is significant, less significant is the effective concentration in the blood.

This type of formulation is not suitable for treating pathologies requiring very fast in vivo availability of GHB such as notably narcolepsy or alcoholic withdrawal.

The solution provided by the present invention gives the possibility of addressing this problem.

Thus, the object of the present invention is to provide a new galenic form based on gamma-hydroxybutyric acid or on one of its salts (notably sodium salt) with which it is possible to circumvent the aforementioned drawbacks.

The object of the present invention is to provide a novel galenic form based on gamma-hydroxybutyric acid or on one of its salts allowing an increase in the dwelling time of the active ingredient in the stomach.

Figure 1:
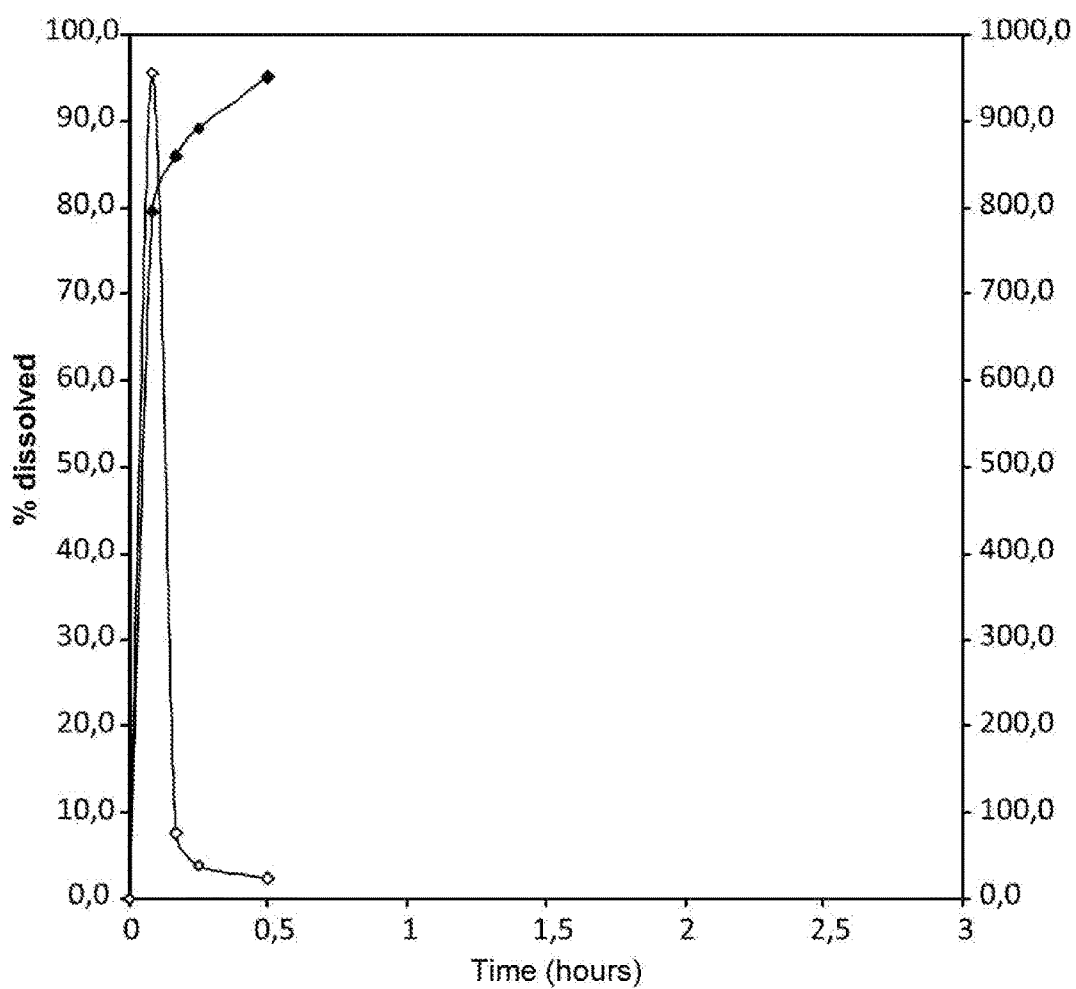
FIG. 1 is a graphic representation of the results of the study of the instantaneous and cumulated dissolution of the immediate release formulations.

The present invention relates to a granule comprising a solid core on which an active ingredient is supported, said active ingredient being selected from gamma-hydroxybutyric acid or one of its pharmaceutically acceptable salts, Said granule further comprising, supported on said solid core, the following compounds:
- one or more compounds which may generate gas evolvement,
- one or several diluents,
- a binder,
- a coating membrane said granule being characterized in that the solid core represents from 15% to 50% by weight based on the total weight of the granule.

Advantageously, the granule according to the present invention consists of:
- 15-25% of solid core,
- 50-60% of active ingredient
- 5-15% of sodium bicarbonate, a gas generator
- 2-18% of Neusilin®, a diluent
- 3-10% of shellac, a binder
- 3-6% of coating membrane The originality of the granules of the invention lies in the use of a particular galenic form intended to increase the dwelling time in the stomach. Indeed, it was observed that the alkalinity of GHB might react in a stomach medium and generate gas evolvement. This effect was combined with the use of a membrane allowing modulation of the diffusion of the active ingredient in situ in the stomach.

The alkalinity of the active ingredients was therefore reinforced by adding alkaline salts mixed with the active ingredient and included at the core of the active ingredient. By immersing the thereby made-up granules in an acid liquid, remanence of the granules is then obtained at the surface of the liquid. The use of the alkaline agent (which may generate gas evolvement) in combination with a coating then allows modulation of the reaction with the same medium and finally ensures a prolonged dwelling time at the absorption sites.

The membrane of the granules according to the present invention allows the active ingredient to slowly diffuse and then react with the stomach medium and finally ensure a prolonged dwelling time at the absorption sites.

The present invention therefore relates to a multiparticulate form of grains or granules. These granules consist of a solid core itself consisting of a solid support or not, on which is deposited a mixture of active ingredient and of different excipients. These excipients are selected from compounds which may generate gas evolvement (alkaline agents) and from diluents. The obtained granule is then surrounded by a membrane, which will allow gradual release of the active ingredient and of the adjuvants required for maintaining the form of the stomach bolus at the surface. Preferentially, the membrane is selected from pH-independent coating excipients and more preferentially shellac.

The present invention consists of providing pharmaceutical formulations comprising the use of several galenic artifacts in order to make each of the techniques encountered during misuses impossible. These formulations based on the aforementioned granules, appear in monolithic form (tablets) or multiparticulate form. Said granules of the invention therefore include several layers of different composition each having a particular functionality.

The expression of "granule" designates a preparation consisting of dry solid grains each forming an aggregate of powder particles with sufficient solidity for allowing diverse handling operations.

From a physical point of view, granules are particle aggregates of diverse crystallized or amorphous powders.

The granules of the present invention are notably intended for oral administration, and more particularly for being swallowed as such.

The granules of the present invention have a characteristic structure of the core-shell type, the core not being of the same nature as the compounds forming the shell.

Thus, these granules have a multi-layer structure. Actually, the active ingredient is deposited on the core and therefore forms a layer (or shell) deposited around this core (or support).

The core of the granules may also be considered as being a support on which the particles of the active ingredient will be attached.

The core consists of solid particles and the active ingredient supported by said core is also in solid form.

The present invention is therefore based on the development of a novel multiparticulate oral form.

The granules of the invention have an active ingredient layer.

The granules of the invention may also include one or more coloring agents. Thus, the coloring agents are selected according to their solubilities in solvents. For example a coloring agent is selected for its solubility in ethanol and another one for its solubility in water. Actually, both of these solvents are solvents customarily used for extracting or solubilizing active ingredients.

The obtained coloration then allows viewing of malevolent additions in a drink, for example for chemical submission.

The granules of the invention may also include one or more metal pigments. The presence of coloring agents and of metal pigments also allows viewing of possible solubilization after milling the pharmaceutical form and subsequently possible ingestion. Also, in the case of chewing, an identical phenomenon is observed.

The coloring agents and the metal pigments may equally be placed in the different layers of the granules of the invention.

Advantageously, an intimate mixture of the coloring agent(s) is carried out with the active ingredient and the metal pigment is used in the surface layer of the composition, i.e. the one which is visible at the surface.

The granules of the invention also comprise in their structure one or more compounds which may generate gas evolvement when the medicinal form is hydrated.

Among the coloring agents of the granules of the invention, mention may notably be made of coloring agents soluble in aqueous solvents and coloring agents soluble in alcoholic solvents.

Among the coloring agents soluble in ethanol, mention may notably be made of the following coloring agents: neutral red, brilliant blue FDC.

Among the coloring agents soluble in water, conventional food coloring agents are used. The coloring agents applied within the scope of the present invention are notably those listed in the 95/45/CE directive as of Jul. 26, 1995 relating to the coloring agents which may be used in foodstuffs (modified by the 2006/33/CE directive of Mar. 20, 2006). Thus, mention may notably be made of the coloring agents E100 to E180.

The coloring agent E131 (patent blue) both soluble in water and in ethanol may also be mentioned.

According to a more preferred embodiment, the metal pigments of the granules of the invention are pigments based on titanium dioxide present at the surface of said granule.

Preferably, the solid core of the granules according to the invention is an insoluble support. As an insoluble support, use is preferably made of polyols, gums, derivatives of silica, calcium or potassium derivatives, mineral compounds such as dicalcium phosphates, tricalcium phosphates and calcium carbonates, saccharose, cellulose derivatives, notably microcrystalline cellulose, ethylcellulose and hydroxypropylmethylcellulose, starch or mixtures thereof.

The granules of the invention comprise a solid core preferably selected from insoluble supports in aqueous or alcoholic solvents. The selection of these insoluble supports forming the solid core of the granules of the invention gives the possibility of avoiding total solubilization of the granule in the case of milling.

The solid core of the granules may also consist of a mixture of compounds, notably a mixture of insoluble supports. Thus mention may notably be made of the mixture formed with saccharose and starch or mineral compounds derived from silica or from calcium.

The solid core may also consist of soluble supports among which mention may be made of certain solid grades of PEG (PEG 4000 or PEG 6000).

The expression "derivatives of silica" designates silica as well as precipitated silicas obtained from alkaline silicates, notably Aerosil®, or further talcum, bentonite or kaolin.

The expression "calcium derivatives" designates crystalline excipients derived from calcium hydroxide, products insoluble in water used in medicine as diluents, or fillers and also abrasives.

The expression "potassium derivatives" designates notably potassium bicarbonate and potassium chloride.

Among the insoluble supports forming the core of the granules of the invention, mention may also be made of derivatives of magnesium (notably carbonates or oxides).

Preferably, spheres of sugar are used as a solid support forming the core of the granules of the invention. These spheres consist of a mixture of saccharose and of starch.

According to a preferred embodiment, the aforementioned granules also comprise a binder. The role of the binder is to bind the particles together, i.e. to enhance cohesion of the granule. Thus, the binders give the possibility of ensuring good cohesion of the active ingredient and of the core in the granules.

Thus, the binders like the active ingredients are deposited around the core of the granules.

As binders, mention may be made of most hydrophilic excipients which provide viscous solutions: arabic gums and tragacanth gums, methylcellulose and carboxymethylcellulose, gelatin, starches, maltodextrins, PEG 4000 and 6000 in an alcoholic solution, polyvidone in an aqueous or alcoholic solution and also solutions of saccharose and of glucose or sorbitol.

The binders of the granules of the invention are preferably selected from the group consisting of starch, saccharose, arabic gum, polyvinylpyrrolidone (PVP or polyvidone), hydroxypropylmethylcellulose (HPMC), shellac, hydroxypropylcellulose (HPC), cellulose, polyols or alginates, polyglycolyzed glycerides (Gelucire®) or macrogolglycerides, notably stearoyl macrogolglycerides, also acrylic derivatives as well as mixtures thereof.

Among the polyols, mention may also notably be made of mannitol, sorbitol, maltitol or xylitol.

According to a particular embodiment, the binders are preferably selected from the group consisting of polyvinylpyrrolidone, shellac, polyols or alginates, polyglycolyzed glycerides (Gelucire) or macrogolglycerides, notably stearoyl macrogolglycerides, as well as mixtures thereof.

It is also possible to use a binder selected from the groups mentioned above for particular properties, for example it may be useful to use as a binder pH-dependent excipients such as EUDRAGIT® L100 or shellac. It may also be possible to select preferentially the use of polyglycolized glycerides (Gelucire®) for their hydrophobicity.

According to a preferred embodiment, the granules of the invention further comprise one or more bitterness agents.

Preferably, said bitterness agent is selected from the group consisting of denatonium benzoate, extracts of gentians, quinine, caffein, brucine, qassin, propyl thiouracil (PROP), phenylthiocarbamide (FTC), astringent compounds such as tannins, grapefruit aromas and bitter cocoa aromas.

The presence of said bittering agent (or bitterness promoter) (ex: Bitrex®—denatonium benzoate) in an intimate mixture with the active ingredient makes absorption by accidental chewing difficult or even impossible, even after extraction and/or solubilization. Actually, said bittering agent is then found solubilized at the same time as the active ingredient, differential separation being very difficult.

The use of such a bitter compound gives the possibility of preventing voluntary administrations or concealed administrations in the form of "cocktails" in water/alcohol mixtures (ice cubes/vodka, etc.).

According to a more preferred embodiment, the solid core of the granules of the invention represent from 15% to 30%, preferably from 20% to 25% by weight based on the total weight of the granule.

Among preferred diluents according to the invention, mention may be made of silica derivatives and notably derivatives of magnesium aluminometasilicate.

Among the derivatives of magnesium aluminometasilicate, mention may notably be made of the product Neusilin® which has an advantage relatively to the very high hygroscopic nature of GHB.

Preferably, the compound which may generate gas evolvement is selected from the group consisting of carbonates and bicarbonates and is notably selected from the group consisting of sodium bicarbonate, sodium carbonate, sodium glycine carbonate, potassium bicarbonate, magnesium carbonate and calcium carbonate.

According to a preferred embodiment, the granules according to the invention comprises sodium bicarbonate as a compound which may generate gas evolvement.

Preferably, the active ingredient of the granules of the invention is the sodium salt of gamma-hydroxybutyric acid.

According to an embodiment, the granules according to the present invention may comprise a membrane consisting of coating excipients for immediate release. Such granules are designated subsequently as immediate release granules.

According to another embodiment, the granules according to the present invention may comprise a membrane consisting of coating excipients for progressive release or sustained over time. Such granules are subsequently designated as progressive sustained release granules.

The present invention also relates to a pharmaceutical composition comprising a mixture of granules as defined above, in which said mixture consists of two groups of granules (A) and (B), the granules (A) and the granules (B) having different release kinetics of the active ingredients.

This specific galenic form consists in the combination of two types of granules having different kinetics. Such a composition gives the possibility of obtaining in vivo results consistent with what is observed in vitro. Moreover, by using a multi-particulate form, it is possible to reduce the strong interindividual variability observed for this active ingredient, comparatively with monolithic forms.

The present invention also relates to a pharmaceutical composition comprising immediate release granules and progressive/sustained release granules.

According to a preferred embodiment, the present invention relates to a pharmaceutical composition comprising immediate release granules in an amount from 5% to 50% by weight, and progressive/sustained release granules in an amount from 50% to 95% by weight. Preferentially, said pharmaceutical composition comprises 25% by weight of immediate release granules and 75% by weight of progressive/sustained release granules.

The present invention also relates to a granule as defined above or to a pharmaceutical composition as defined above, for its use for treating catalepsy in narcoleptic patients, or for its use in alcoholic withdrawal.

The present invention also relates to a granule as defined above, or to a pharmaceutical composition as defined above, for its use for preventing and/or treating fibromyalgia, for preventing alcoholic recidivisms and maintaining abstinence, or further for treating anxiety in alcoholics.

The present invention also relates to a method for preparing a granule as defined above, in that it comprises a step for applying the active ingredient by dusting on the solid core.

According to a preferred embodiment of the method of the invention, the active ingredient is mixed with compounds which may generate gas evolvement, diluents, optional coloring agents, and optional metal pigments before the step for application on the solid core by dusting.

The method of the invention may also comprise, after the dusting step, a step for coating the granule, notably by depositing by lamination the coating agent in the form of a film on the granule, if necessary followed by a step for mixing with a lubricant and/or a flavoring agent and/or a sweetener and/or a coloring agent or metal pigment.

The structure of the granules of the invention is related to the application of this particular method with which granules with a core-shell structure may be obtained.

By carrying out comparative tests for preparing granules by a direct granulation method with different excipients customarily used in granulation, it was noticed that the obtained results concerning the actual granule are satisfactory as regards the aspect, the brittleness and the dissolution. However, the granules obtained by such a method have a very high specific surface area requiring large amounts of coating polymers according to the conventionally used techniques.

Thus, the granules of the present invention are characterized in that they have a lowered specific surface area, moreover, from an aspect point of view, they are relatively smooth and have a rather regular shape.

The aforementioned dusting step of the method for preparing the granules of the invention may also comprise a step for spraying an alcoholic or hydro-alcoholic or aqueous solution of a binder.

This spraying step and dusting step are preferably carried out simultaneously or alternately.

Preferably, the aforementioned dusting step is carried out concomitantly with a step for spraying a binder in the form of a solution.

The combination of these steps gives the possibility of ensuring good cohesion of the active ingredient on the core of the granules.

An advantageous application of the method of the invention thus consists of applying the active ingredient as a powder on the aforementioned particulate support (or core of the granules) by alternating sequences for spraying the binder in the form of a solution.

The method of the invention may also comprise, after the previous step, one or more steps for coating the granule, notably by depositing by lamination the coating agent(s) as films on the granule.

The small specific surface area of the granules of the invention thus allows in the case of coating, a reduction in the amount used of coating agent and therefore less dilution of the active ingredient in said coated granules.

A preferred embodiment of the method of the invention consists in a method comprising, after the coating step, a step for mixing with a lubricant and/or an aroma and/or a sweetener, the latter may themselves be prepared as granules in order to be finally mixed with the active granules.

All the lubricants, flavoring agents and sweeteners may also be added before the aforementioned dusting step.

EXAMPLES

I—Procedures for Preparing the Granules According to the Invention

The active ingredient is mixed for fifteen minutes with the compound capable of generating gas evolvement and the diluent in a mixer by inversion. The obtained mixture is then milled on a mill of the Forplex F1 type so as to obtain an adequate grain size. The active mixture is then deposited on neutral supports (solid core). The granules are placed in a conventional turbine, the mixture is deposited by dusting, by alternating dusting phases and phases for spraying a binding solution.

At the end of this dusting step, a phase for drying is carried out in order to remove the solvents used during the previous step.

It is then proceeded with the coating step. For this, the granules from the previous step are placed in a fluidized air bed of the GPCG30 type and the coating solution (for the membrane) is then sprayed on the mass of granules being fluidized.

After a last drying step, it is proceeded with the lubrication phase, the ultimate step of the method, which consists in packaging them as sticks, bags, ampoules or flasks.

II—Examples of Formulations According to the Invention

Example 1 (Immediate Release)

Formula No. 1

| Materials | % |
|---|---|
| GHB (hydrate salt) | 57.60 |
| Sodium bicarbonate | 8.64 |
| Neusilin ® UFL2 (diluent) | 5.18 |

-continued

| Formula No. 1 | |
|---|---|
| Materials | % |
| Whitened dewaxed shellac (binder) | 4.60 |
| Sugar spheres (solid core) | 20.57 |
| Sepifilm LP014 (protective membrane against humidity) | 2.90 |
| Talcum | 0.50 |
| Theoretical mass | 100.0 |

Example 2 (Modified Release)

| Formula No. 2 | |
|---|---|
| Materials | % |
| GHB (hydrate salt) | 56.49 |
| Sodium bicarbonate | 8.47 |
| Neusilin ® UFL2 (diluent) | 5.09 |
| Whitened dewaxed shellac (binder) | 7.12 |
| Sugar spheres (solid core) | 20.08 |
| Sepifilm LP014 (protective membrane against humidity) | 0.76 |
| Pharmacoat 603 (diffusion membrane) | 1.15 |
| Talcum | 0.85 |
| Theoretical mass | 100.0 |

Example 3 (50/50 Mixture)

| Formula No. 3 | |
|---|---|
| Materials | % |
| GHB (hydrate salt) | 57.04 |
| Sodium bicarbonate | 8.56 |
| Neusilin ® UFL2 (diluent) | 5.13 |
| Whitened dewaxed shellac (binder) | 5.87 |
| Sugar spheres (solid core) | 20.32 |
| Sepifilm LP014 (protective membrane against humidity) | 1.82 |
| Pharmacoat 603 (diffusion membrane) | 0.58 |
| Talcum | 0.68 |
| Theoretical mass | 100.0 |

Example 4 (Immediate Release)

| Formula No. 4 | |
|---|---|
| Materials | % |
| GHB (hydrate salt) | 56.47 |
| Sodium bicarbonate | 8.47 |
| Neusilin ® UFL2 (diluent) | 5.08 |
| Whitened dewaxed shellac (binder) | 6.56 |
| Sugar spheres (solid core)) | 19.88 |
| Protective coating | 3.04 |
| Talcum | 0.50 |
| Theoretical mass | 100.0 |

Example 5 (Modified Release)

| Formula No. 5 | |
|---|---|
| Materials | % |
| GHB (hydrate salt) | 54.75 |
| Sodium bicarbonate | 8.22 |
| Neusilin ® UFL2 (diluent) | 4.91 |
| Whitened dewaxed shellac (binder) | 9.79 |
| Sugar spheres (solid core) | 19.27 |
| Protective coating | 1.89 |
| Talcum | 1.18 |
| Theoretical mass | 100.0 |

Example 6 (25-75 Mixture of Granules)

| Formula No. 6 | |
|---|---|
| Materials | % |
| GHB (hydrate salt) | 55.17 |
| Sodium bicarbonate | 8.28 |
| Neusilin ® UFL2 (diluent) | 4.95 |
| Whitened dewaxed shellac (binder) | 9.00 |
| Sugar spheres (solid core) | 19.42 |
| Protective coating | 2.16 |
| Talcum | 1.02 |
| Theoretical mass | 100.0 |

III—Stability and Dissolution Studies

Analytical Method

The presented formulations were tested analytically and their dissolution was studied in order to anticipate in vitro the in vivo behavior of the different formulations. The retained method is the following:

The tests are subject to constant stirring of 100 rpm in 900 of 0.1N hydrochloric acid at 37° C. in a dissolution apparatus equipped with blades (USP apparatus 2). Samples are taken by means of a sample collector, at 5, 10, 15 and 30 mins, and then analyzed in HPLC.

The results of the dissolution tests carried out on the different formulations are shown below.

The behavior over time of the formulations was also studied: sticks as well as ampoules were made from the presented formulations and after distribution in weathering enclosures, a stability study was conducted according to the ICH standards in effect.

The results of these studies are shown below.

For the two shown packagings, the absence of a significant modification of the evaluated parameters may be ascertained. The formulations demonstrate a perfectly acceptable stability with regard to the ICH standards.

III.1. Results with Formula No. 1 According to Example 1

Results in Ampoules of 1.75 g at 25° C./60% RH

|  | Test points | | | |
| --- | --- | --- | --- | --- |
|  | T0 | T6 months | T12 months | T18 months |
| Characteristics of the granules | | | | |
| Color | Whitish | Whitish | Whitish | Whitish |
| Shape | Spherical | Spherical | Spherical | Spherical |
| Aspect | Homogeneous | Homogeneous | Homogeneous | Homogeneous |
| | | Dosage | | |
| Content (g/ampoule) | 1.753 | 1.753 | 1.736 | 1.758 |
| %/theory | 100.2 | 100.2 | 99.2 | 100.5 |
| Dosage of the impurities | | | | |
| Total sum (%) | < LD (detection limit) | < LQ (quantification limit | < LQ | < LD |
| Dissolution test | | | | |
| Time (min) | | Dissolved % | | |
| 5 | — | 88.7 | 90.1 | 87.3 |
| 10 | — | 92.5 | 97.9 | 94.9 |
| 15 | 93.5 | 94.6 | 98.6 | 98.2 |
| 30 | 97.8 | 97.1 | 99.9 | 99.6 |

The results of the stability study are satisfactory considering the ICH standards.

Results in Ampoules of 1.75 g at 40° C./75% RH

|  | Test point | | | |
| --- | --- | --- | --- | --- |
|  | T0 | T2 months | T3 months | T6 months |
| Characteristics of the granules | | | | |
| Color | Whitish | Whitish | Whitish | Whitish |
| Shape | Spherical | Spherical | Spherical | Spherical |
| Aspect | Homogeneous | Homogeneous | Homogeneous | Homogeneous |
| | | Dosage | | |
| Content (g/ampoule) | 1.753 | 1.765 | 1.753 | 1.723 |
| %/theory | 100.2 | 100.9 | 100.2 | 98.5 |
| Dosage of the impurities | | | | |
| Total sum (%) | < LD | < LQ | < LQ | < LD |
| Dissolution test | | | | |
| Time (min) | | Dissolved % | | |
| 5 | — | — | — | 77.0 |
| 10 | — | — | — | 88.3 |
| 15 | 93.5 | 95.9 | 90.6 | 91.8 |
| 30 | 97.8 | 99.4 | 93.3 | 96.8 |

The results of the stability study are satisfactory considering the ICH standards.

III.2. Results with Formula No. 3 According to Example 3

Results in Ampoules of 1.50 g at 25° C./60% RH

|  | Test points | | | |
| --- | --- | --- | --- | --- |
|  | T0 | T5 months | T9 months | T12 months |
| Characteristics of the granules | | | | |
| Color | Whitish | Whitish | Whitish | Whitish |
| Shape | Spherical | Spherical | Spherical | Spherical |
| Aspect | Homogeneous | Homogeneous | Homogeneous | Homogeneous |
| Dosage | | | | |
| Content (g/ampoule) | 1.502 | 1.485 | 1.496 | 1.515 |
| %/theory | 100.1 | 99.0 | 99.7 | 101.0 |
| Dosage of the impurities | | | | |
| Total sum (%) | < LD | < LD | < LD | < LD |
| Residual solvents | | | | |
| Ethanol (ppm) | 414 | < LD | < LQ | < LQ |
| Dissolution test | | | | |
| Time (min) | Dissolved % | | | |
| 5 | 50.8 | 50.4 | 50.2 | 49.4 |
| 15 | 55.4 | 56.2 | 56.0 | 54.4 |
| 60 | 72.5 | 72.8 | 73.4 | 72.0 |
| 120 | 85.3 | 87.4 | 88.4 | 87.0 |
| 180 | 92.1 | 94.6 | 96.1 | 94.5 |

The results of the stability study are satisfactory considering the ICH standards.

Results in Ampoules of 1.50 g at 40° C./75% RH

|  | Test points | | | |
| --- | --- | --- | --- | --- |
|  | T0 | T1 month | T3 months | T7 months |
| Characteristics of the granules | | | | |
| Color | Whitish | Whitish | Whitish | Whitish |
| Shape | Spherical | Spherical | Spherical | Spherical |
| Aspect | Homogeneous | Homogeneous | Homogeneous | Homogeneous |
| Dosage | | | | |
| Content (g/ampoule) | 1.502 | 1.485 | 1.506 | 1.500 |
| %/theory | 100.1 | 99.0 | 100.3 | 100.0 |
| Dosage of the impurities | | | | |
| Total sum (%) | < LD | < LQ | < LQ | < LD |
| Residual solvents | | | | |
| Ethanol (ppm) | 414 | 205 | < LQ | < LQ |
| Dissolution tests | | | | |
| Time (min) | Dissolved % | | | |
| 5 | 50.8 | 49.2 | 49.0 | 49.3 |
| 15 | 55.4 | 55.5 | 56.5 | 55.2 |
| 60 | 72.5 | 73.0 | 72.3 | 71.0 |
| 120 | 85.3 | 86.1 | 86.8 | 86.8 |
| 180 | 92.1 | 94.5 | 93.8 | 95.7 |

The results of the stability tests are satisfactory considering the ICH standards.

IV—Results of Dissolution In Vitro

|  | SMO.IR A001 (Example 1) | SMO.IR A002 (Example 4) |
|---|---|---|
| 0 | 0.0 | 0.0 |
| 0.0833 | 88.7 | 79.6 |
| 0.1667 | 92.5 | 86.0 |
| 0.25 | 94.6 | 89.2 |
| 0.5 | 97.1 | 95.1 |

Sustained Release

| | Dissolved % | |
|---|---|---|
| Time (h) | SMO.SR A001 (Example 2) | SMO.SR A002 (Example 5) |
| 0 | 0.0 | 0.0 |
| 0.25 | 9.6 | 10.5 |
| 0.5 | 20.6 | 22.4 |
| 1 | 41.5 | 45.8 |
| 2 | 72.0 | 75.6 |
| 3 | 87.0 | 90.7 |
| 4 | 94.8 | |

50/50 Mixture

| Time (h) | Dissolved % SMO.MR A001 (Example 3) |
|---|---|
| 0 | 0.0 |
| 0.0833 | 50.8 |
| 0.25 | 55.4 |
| 0.5 | 59.0 |
| 1 | 72.5 |
| 2 | 85.3 |
| 3 | 92.1 |

An in vitro/in vivo relationship study was conducted on the test formulations and references. The test formulations were developed within the scope of the present invention and appear as microgranules as described earlier.

Two references of oral formulations exist on the market: ALCOVER® and XYREM®. They are in liquid form in a flask. The bioequivalences of the microgranules, versus solutions were studied in clinical studies with the following doses: 1,750 and 2,250 mg.

The first goal of the study is to describe the intestinal absorption kinetics of gamma-hydroxybutryic acid in humans, after its oral administration as a solution or as microgranules, in order to determine whether its dissolution profile and rate in vitro from microgranules have an influence on the profile of the plasma concentrations of gamma-hydroxybutric acid as well as on its pharmacokinetic parameters.

The second goal is to analyze the in vivo absorption kinetics of the microgranules and to compare them with those of the oral form solutions on the market.

Exposure to gamma-hydroxybutyric acid (AUCinf) is not dose-dependent for the tested doses (1,750-2,250 mg), absorption and exposure have good proportionality relatively to the doses, which allows determination and comparison of the absorption kinetics at both dosages.

The oral absorption kinetics expressed as a % of cumulated absorbed doses and as absorption rates versus time were calculated by a compartmental pharmacokinetic deconvolution method (Wagner J G, Nelson E.) for solutions of ALCOVER® and XYREM® and for the microgranules, administered to healthy volunteers at unit doses of 1,750 mg and 2,250 mg (in two separate studies).

In the cases of solutions and microgranules, the cumulative systemic absorption kinetics of gamma-hydroxybutryic acid are then analyzed in order to mathematically characterize their profiles by calculating the constants of the equations which describe the systemic absorption of gamma-hydroxybutyric acid (cumulative curves and rates versus time). The absorption models as well as the equations are reported.

For the solutions tested at 1,750 and 2,250 mg, the absorption kinetics are very fast; the total duration of the absorption mechanism is less than 1 hour.

The time required for 50% absorption of the dose (T50%) is very short from 0.21 to 0.28 hour, the absorption maximum rates (314 to 362%/h) are observed earlier, at 0.33 hour. All the absorption mechanisms follow first order kinetics; the absorption constants are very high: from 4.5 to 9.3 H-1, confirming very fast oral absorption of the gamma-hydroxybutryic acid solutions.

For the microgranules, the cumulative absorption kinetics, the absorption rates versus time as well as the parameters may be superposed to those obtained after administration of both solutions, regardless of the dosage; the constants of the equations describing the absorption kinetics are similar.

The processes for in vivo dissolution of the microgranules are so fast that they do not have any influence on the profiles and kinetic parameters for absorption of gamma-hydroxybutric acid.

The kinetics for in vitro dissolution of gamma-hydroxybutric acid from microgranules are very fast, more than 85% of the dose is dissolved in less than 5 minutes under all tested physiological pH conditions (pH from 1.2 to 6.8) regardless of the in vitro conditions.

The very high dissolution rate of gamma-hydroxybutric acid from microgranules explains the absence of any difference in absorption rates in vivo between solutions and microgranules.

The dissolution of the microgranules does not affect the absorption kinetics of gamma-hydroxybutric acid, which may be superposed to that of solutions available on the market.

The absorption parameters were studied according to the compartmental pharmacokinetic deconvolution method of Wagner J G., Nelson E. [J. Pharm. Sci. 1968; 53(11):1392-1403]. This pharmacokinetic method based on the calculation of areas under curves of average plasma concentrations versus time and of the terminal elimination slope of the average curves gives the possibility of calculating at each instant of the plasma kinetics, the dose percentage having entered the systemic circulation relatively to the total amount having entered at the end of the absorption; this method therefore results in 0 to 100% characterization of the profile of the systemic entrance of the tested formulations. The condition for applying the method was checked: the average terminal elimination slope calculated by semi-logarithmic regression on the linear portion of the plasma curves from 1.5 to 4 hours for the microgranules is similar to that of solutions and corresponds to the very short plasma half-life (T½) of gamma-hydroxybutric acid: see table below.

|  | ALCOVER1750 | XYREM1750 | MICROG1750 | ALCOVER2250 | MICROG2250 |
|---|---|---|---|---|---|
| Slope (H-1) | 1.06 | 1.11 | 0.85 | 1.03 | 1.02 |
| T½ (H) | 0.65 | 0.62 | 0.81 | 0.68 | 0.68 |

The following curves and tables show the absorption percentages as well as the absorption ratios of the test forms and references.

Figure 6:
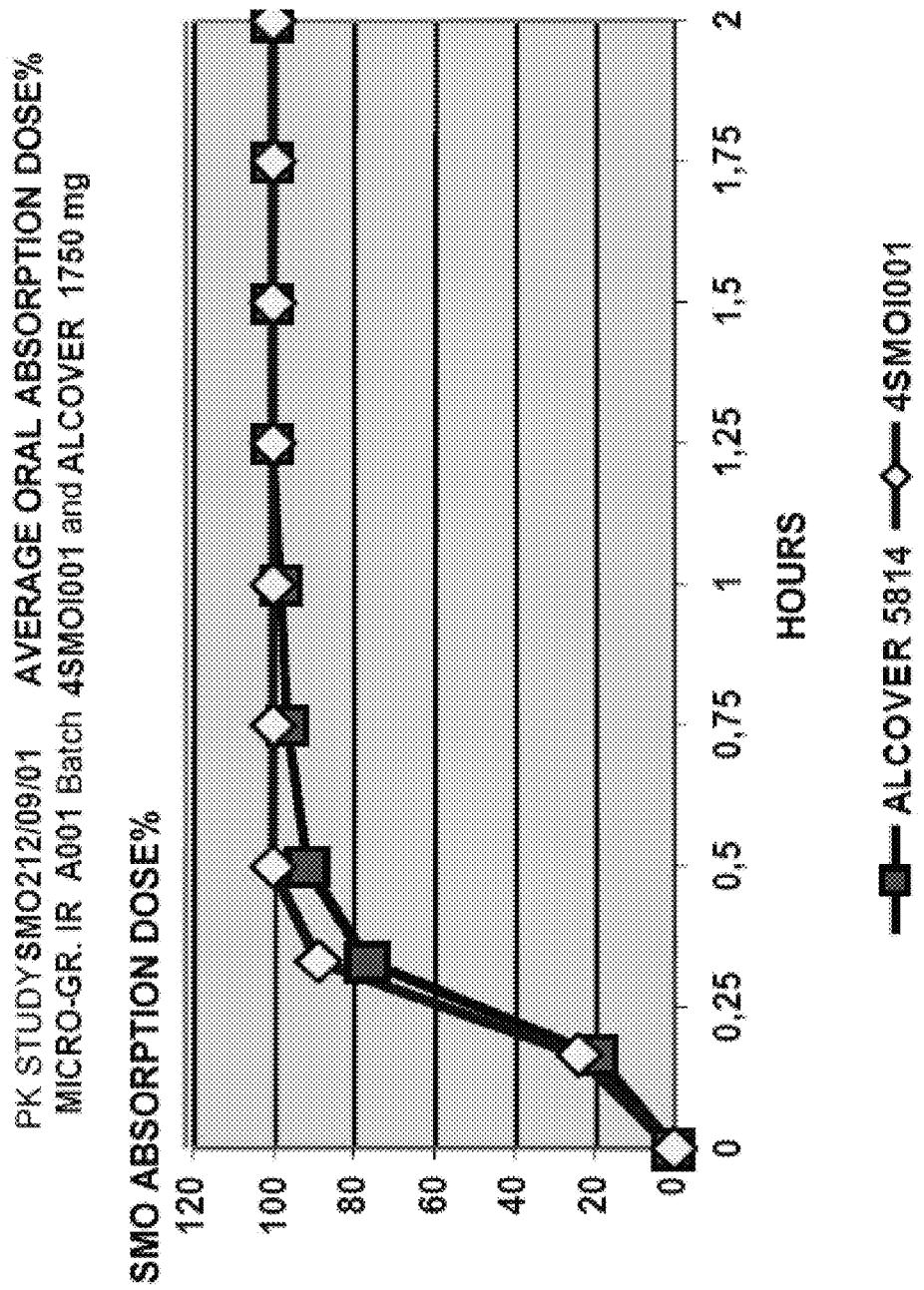
FIG. 6 is a graphic representation of absorption percentage data from the study of the 1,750 mg dosage of various samples (Alcover reference)
Figure 7:
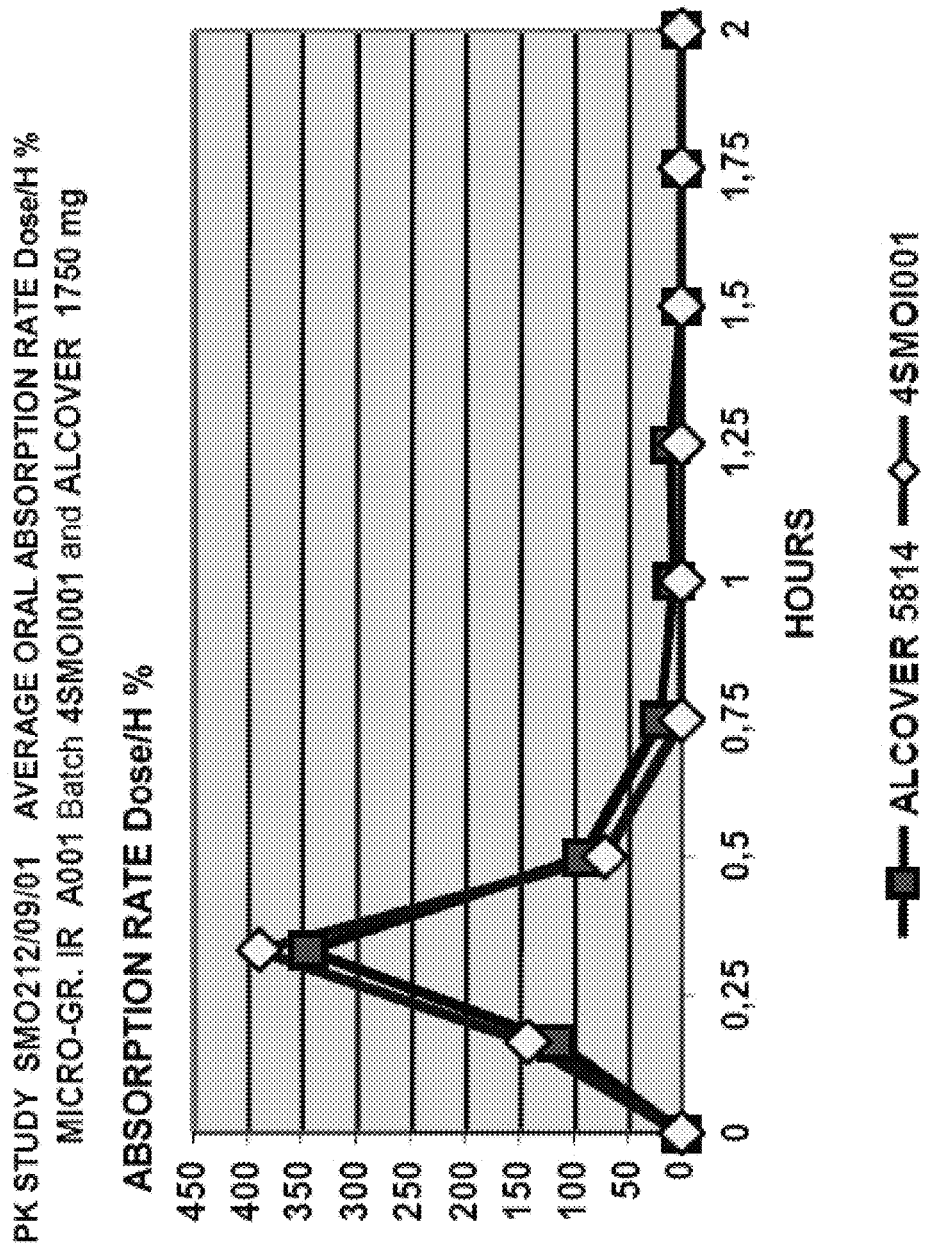
FIG. 7 is a graphic representation of absorption ratio data from the study of the 1,750 mg dosage of various samples (Alcover reference)

Dosage 1,750 mg: Alcover reference (the results being illustrated in the following tables and FIGS. 6 and 7):

| HUMAN IN VIVO - PK STUDY SMO212/09/01 ABSORPTION RESULTS: DOSE % | | |
|---|---|---|
| TIME (HOURS) | SOLUTION ALCOVER 5814 | MICROG-IR 4SMOI001 |
| 0 | 0 | 0 |
| 0.17 | 19.18 | 23.62 |
| 0.33 | 76.25 | 88.37 |
| 0.50 | 91.13 | 100.00 |
| 0.75 | 95.97 | 100.00 |
| 1.00 | 97.68 | 100.00 |
| 1.25 | 100.00 | 100.00 |
| 1.50 | 100.00 | 100.00 |
| 1.75 | 100.00 | 100.00 |
| 2.00 | 100.00 | 100.00 |
| 2.50 | | |

| HUMAN IN VIVO - PK STUDY SMO212/09/01 ABSORPTION RESULTS: DOSE/H % | | |
|---|---|---|
| TIME (HOURS) | SOLUTION ALCOVER 5814 | MICROG-IR 4SMOI001 |
| 0 | 0 | 0 |
| 0.17 | 115.07 | 141.67 |
| 0.33 | 342.57 | 388.66 |
| 0.50 | 89.26 | 69.78 |
| 0.75 | 19.36 | 0.00 |
| 1.00 | 6.81 | 0.00 |
| 1.25 | 9.30 | 0.00 |
| 1.50 | 0.00 | 0.00 |
| 1.75 | 0.00 | 0.00 |
| 2.00 | 0.00 | 0.00 |
| 2.50 | | |

The absorption kinetics of gamma-hydroxybutric acid (dose % and rate) have the same profiles and may be superposed.

The IR microgranules do not induce any delay or any modification of the absorption process of gamma-hydroxybutric acid relatively to the Alcover reference solution. Dissolution in vivo in the stomach is very fast and total.

Figure 8:
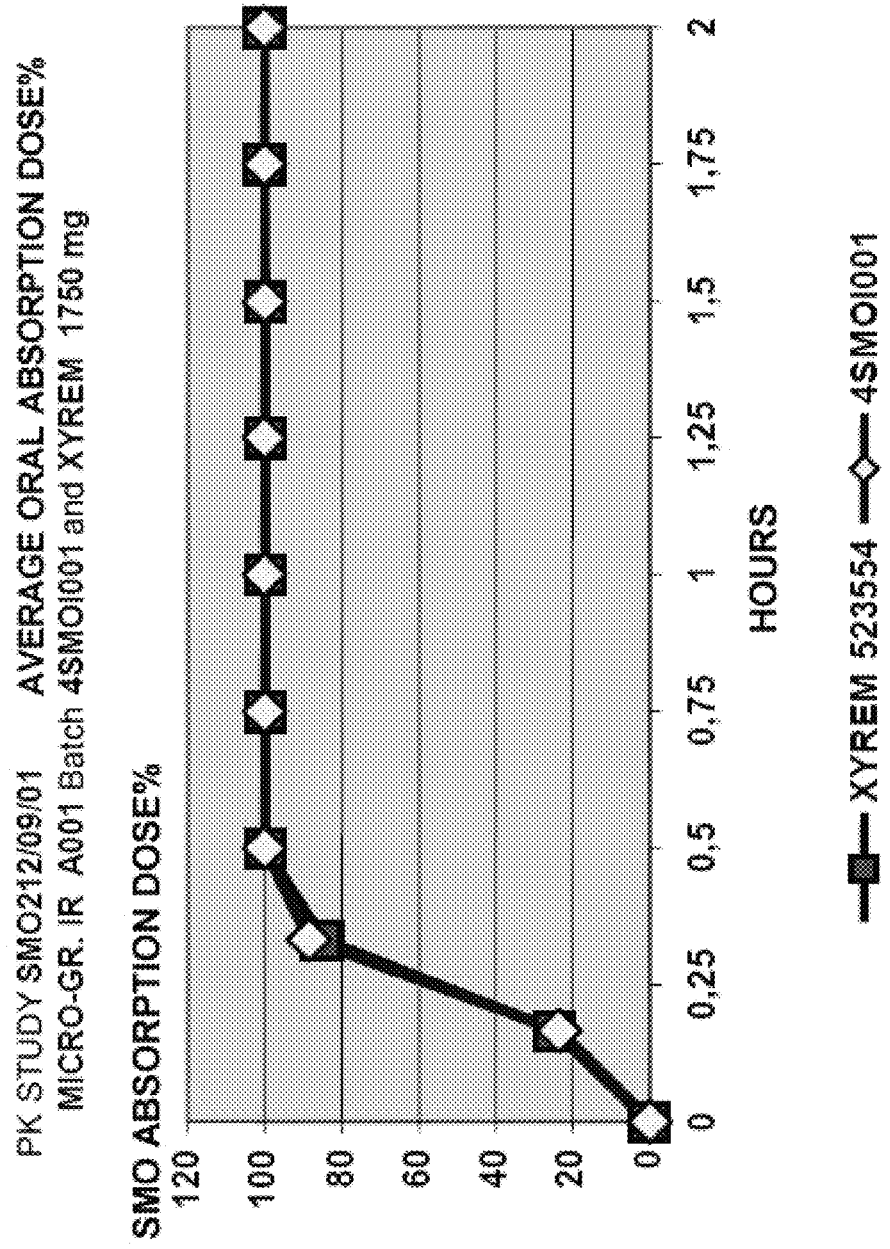
FIG. 8 is a graphic representation of absorption percentage data from the study of the 1,750 mg dosage of various samples (Xyrem reference)
Figure 9:
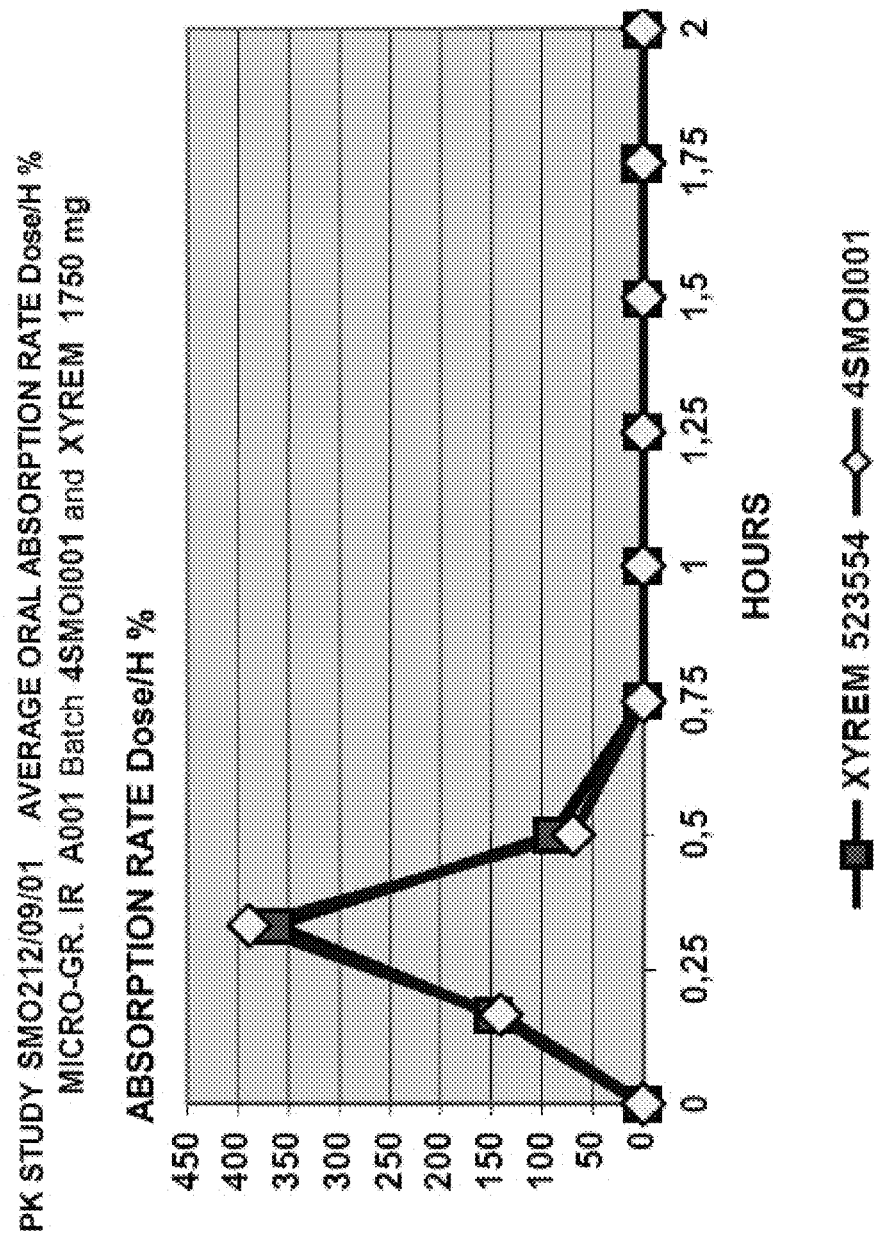
FIG. 9 is a graphic representation of absorption ratio data from the study of the 1,750 mg dosage of various samples (Xyrem reference)

Dosage 1,750 mg: Xyrem reference (the results being illustrated in the following tables and FIGS. 8 and 9):

| HUMAN IN VIVO - PK STUDY SMO212/09/01 ABSORPTION RESULTS: DOSE % | | |
|---|---|---|
| TIME (HOURS) | SOLUTION XYREM 523554 | MICROG-IR 4SMOI001 |
| 0 | 0 | 0 |
| 0.17 | 24.61 | 23.62 |
| 0.33 | 84.87 | 88.37 |
| 0.50 | 99.67 | 100.00 |
| 0.75 | 99.67 | 100.00 |
| 1.00 | 99.67 | 100.00 |
| 1.25 | 99.67 | 100.00 |
| 1.50 | 99.67 | 100.00 |
| 1.75 | 100.00 | 100.00 |
| 2.00 | 100.00 | 100.00 |
| 2.50 | | |

| HUMAN IN VIVO - PK STUDY SMO212/09/01 ABSORPTION RESULTS: DOSE/H % | | |
|---|---|---|
| TIME (HOURS) | SOLUTION XYREM 523554 | MICROG-IR 4SMOI001 |
| 0 | 0 | 0 |
| 0.17 | 147.64 | 141.79 |
| 0.33 | 361.67 | 388.98 |
| 0.50 | 88.80 | 69.34 |
| 0.75 | 0.00 | 0.00 |
| 1.00 | 0.00 | 0.00 |
| 1.25 | 0.00 | 0.00 |
| 1.50 | 0.00 | 0.00 |
| 1.75 | 1.32 | 0.00 |
| 2.00 | 0.00 | 0.00 |
| 2.50 | | |

The absorption kinetics of gamma-hydroxybutric acid (Dose % and rate) have the same profiles and may be superposed.

The IR microgranules do not induce any delay or any modification of the absorption process of gamma-hydroxybutric acid relatively to the Xyrem reference solution. Dissolution in vivo in the stomach is very fast and total.

Figure 10:
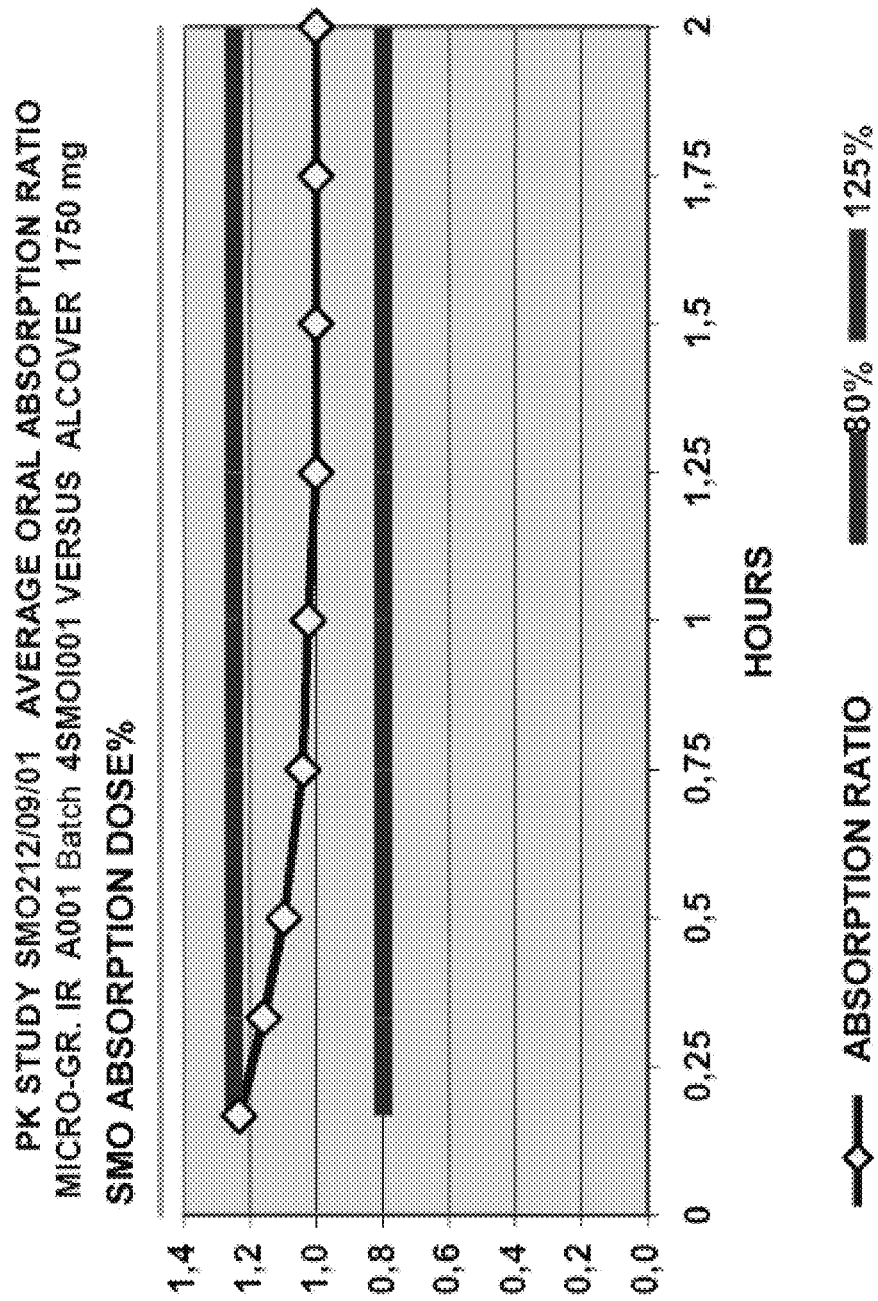
FIG. 10 is a graphic representation of the ratio R data of the absorption profiles of the IR 1,750 mg microgranules (Alcover reference)

Dosage 1,750 mg: Microgranule formulation versus Alcover and Xyrem (the results being illustrated in the following table and FIG. 10):

| PK STUDY SMO212/09/01 AVERAGE ORAL ABSORPTION RATIO MICRO-GR. IR A001 Lot 4SMOI001 VERSUS ALCOVER 1750 mg | |
|---|---|
| HOURS | MICROG-IR ABSORPTION RATIO |
| 0 | |
| 0.17 | 1.23 |
| 0.33 | 1.16 |
| 0.50 | 1.10 |
| 0.75 | 1.04 |
| 1.00 | 1.02 |
| 1.25 | 1.00 |

PK STUDY SMO212/09/01
AVERAGE ORAL ABSORPTION RATIO
MICRO-GR. IR A001 Lot 4SMOI001
VERSUS ALCOVER 1750 mg

| HOURS | MICROG-IR ABSORPTION RATIO |
|---|---|
| 1.50 | 1.00 |
| 1.75 | 1.00 |
| 2.00 | 1.00 |

Figure 11:
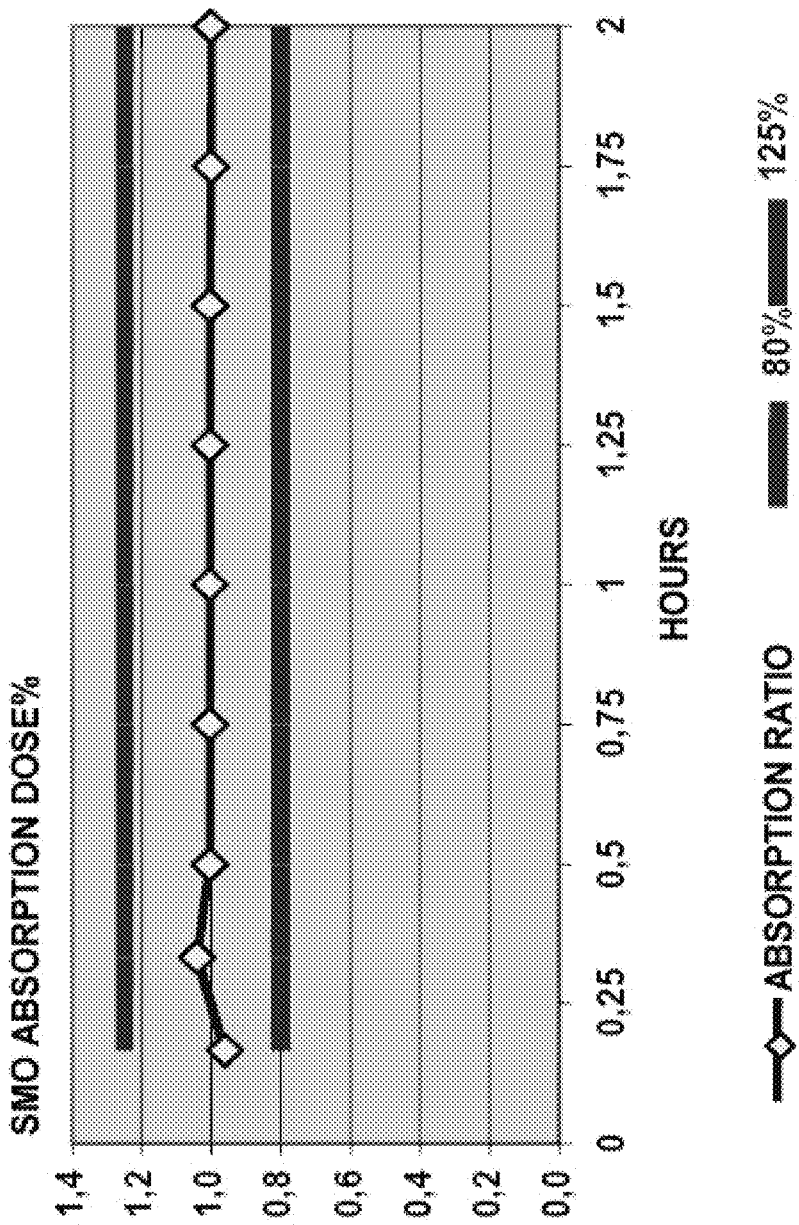
FIG. 11 is a graphic representation of the ratio R data of the absorption profiles of the IR 1,750 mg microgranules (Xyrem reference)

The ratio R of the absorption profiles of the IR 1750 mg microgranules and of the Alcover® solution is included between the values 0.8 and 1 (the results being illustrated in the following table and FIG. 11).

PK STUDY SMO212/09/01
AVERAGE ORAL ABSORPTION RATIO
MICRO-GR. IR A001 Batch 4SMOI001
VERSUS XYREM 1750 mg

| HOURS | MICROG-IR ABSORPTION RATIO |
|---|---|
| 0 | |
| 0.17 | 0.96 |
| 0.33 | 1.04 |
| 0.50 | 1.00 |
| 0.75 | 1.00 |
| 1.00 | 1.00 |
| 1.25 | 1.00 |
| 1.50 | 1.00 |
| 1.75 | 1.00 |
| 2.00 | 1.00 |

The ratio of the absorption profiles of the IR 1750 mg microgranules and of the XYREM® solution is included between the values 0.8 and 1.2.

Figure 12:
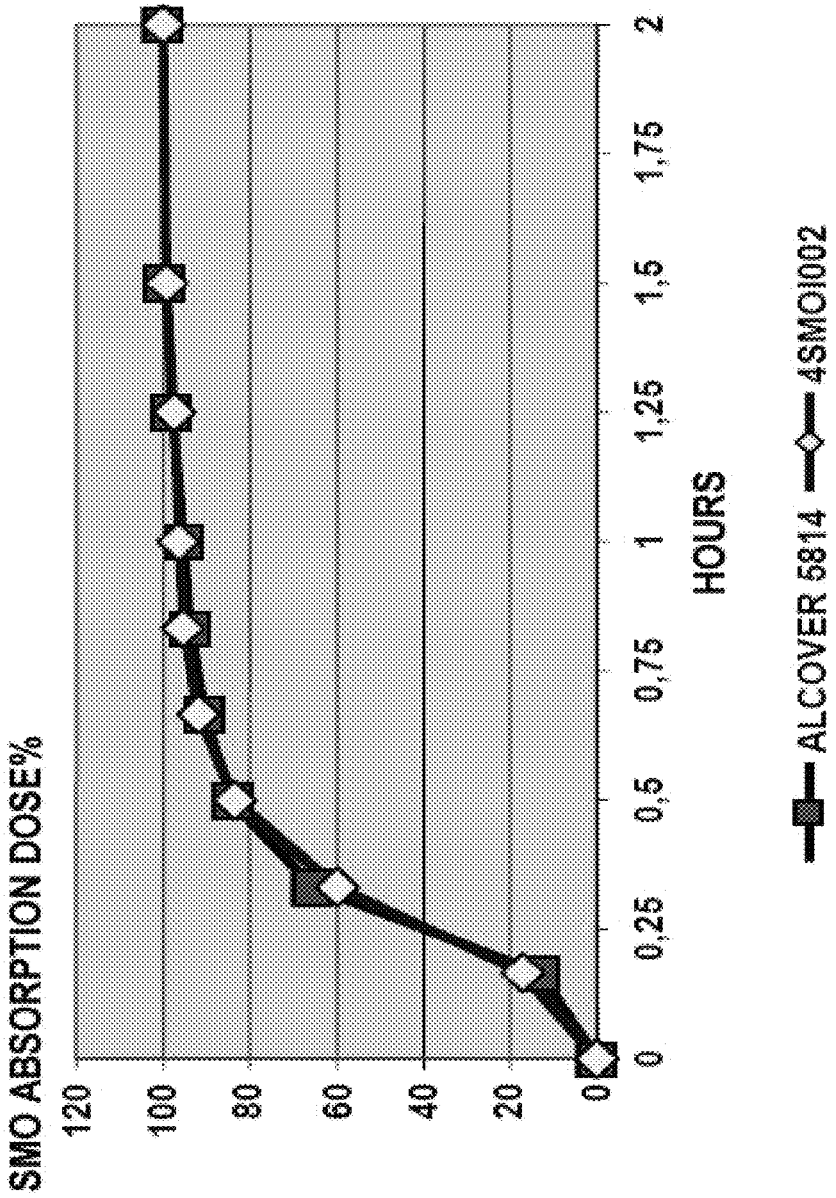
FIG. 12 is a graphic representation of absorption percentage data from the study of the 2,250 mg dosage of various samples (Alcover reference)
Figure 13:
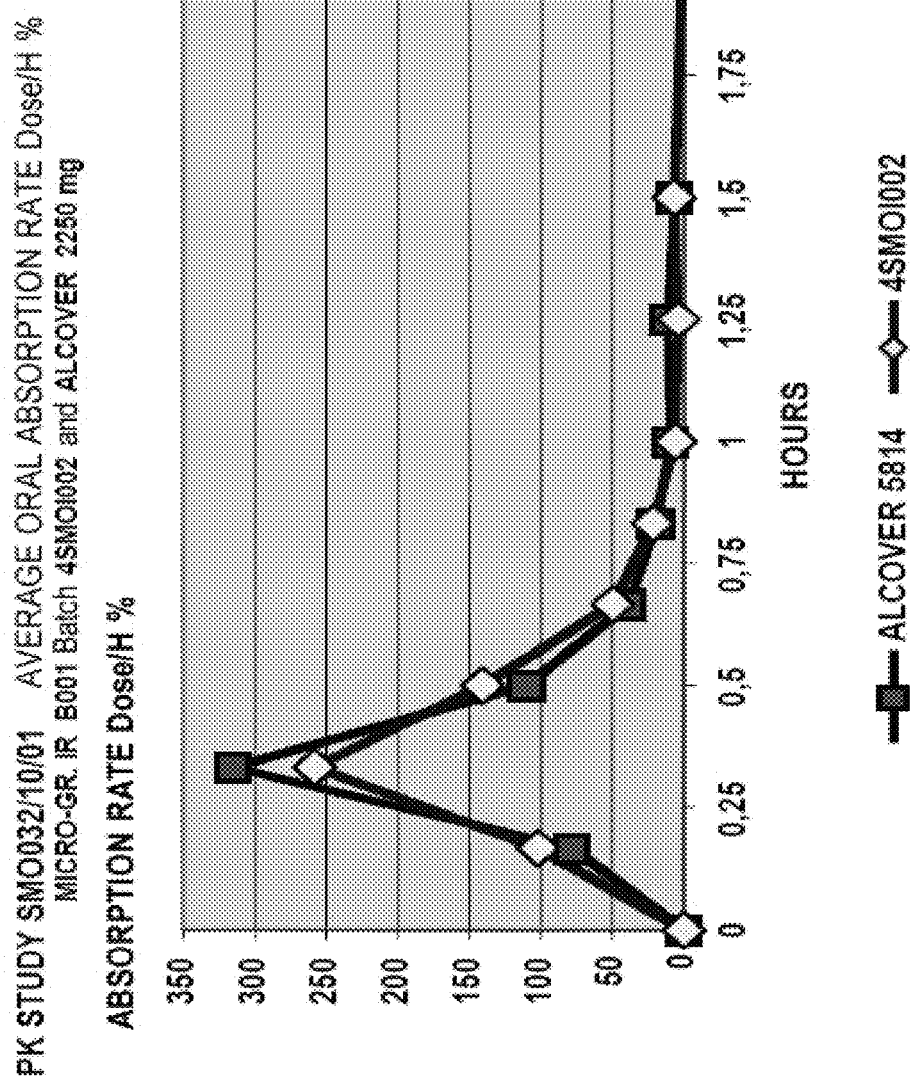
FIG. 13 is a graphic representation of absorption ratio data from the study of the 2,250 mg dosage of various samples (Alcover reference)

Dosage 2,250 mg: Alcover reference (the results being illustrated in the following tables and FIGS. 12 and 13):

HUMAN IN VIVO - PK STUDY
SMO032/10/11
ABSORPTION RESULTS: DOSE %

| TIME (HOURS) | SOLUTION ALCOVER 5814 | MICROG-IR 4SMOI002 |
|---|---|---|
| 0 | 0 | 0 |
| 0.17 | 13.09 | 17.05 |
| 0.33 | 65.56 | 59.99 |
| 0.50 | 83.90 | 83.52 |
| 0.75 | 90.33 | 91.79 |
| 1.00 | 93.59 | 95.41 |
| 1.25 | 95.18 | 96.46 |
| 1.50 | 97.99 | 97.44 |
| 1.75 | 99.63 | 99.22 |
| 2.00 | 100.00 | 100.00 |
| 2.50 | 100.00 | 100.00 |

HUMAN IN VIVO - PK STUDY
SMO212/09/01
ABSORPTION RESULTS: DOSE/H %

| TIME (HOURS) | SOLUTION ALCOVER 5814 | MICROG-IR 4SMOI001 |
|---|---|---|
| 0 | 0 | 0 |
| 0.17 | 115.07 | 141.67 |
| 0.33 | 342.57 | 388.66 |
| 0.50 | 89.26 | 69.78 |
| 0.75 | 19.36 | 0.00 |
| 1.00 | 6.81 | 0.00 |
| 1.25 | 9.30 | 0.00 |
| 1.50 | 0.00 | 0.00 |
| 1.75 | 0.00 | 0.00 |
| 2.00 | 0.00 | 0.00 |
| 2.50 | | |

The absorption kinetics of gamma-hydroxybutric acid (dose % and rate) have the same profiles and may be superposed.

The IR microgranules do not induce any delay or any modification of the absorption process of gamma-hydroxybutric acid relatively to the Alcover reference solution. Dissolution in vivo in the stomach is very fast and total.

Figure 14:
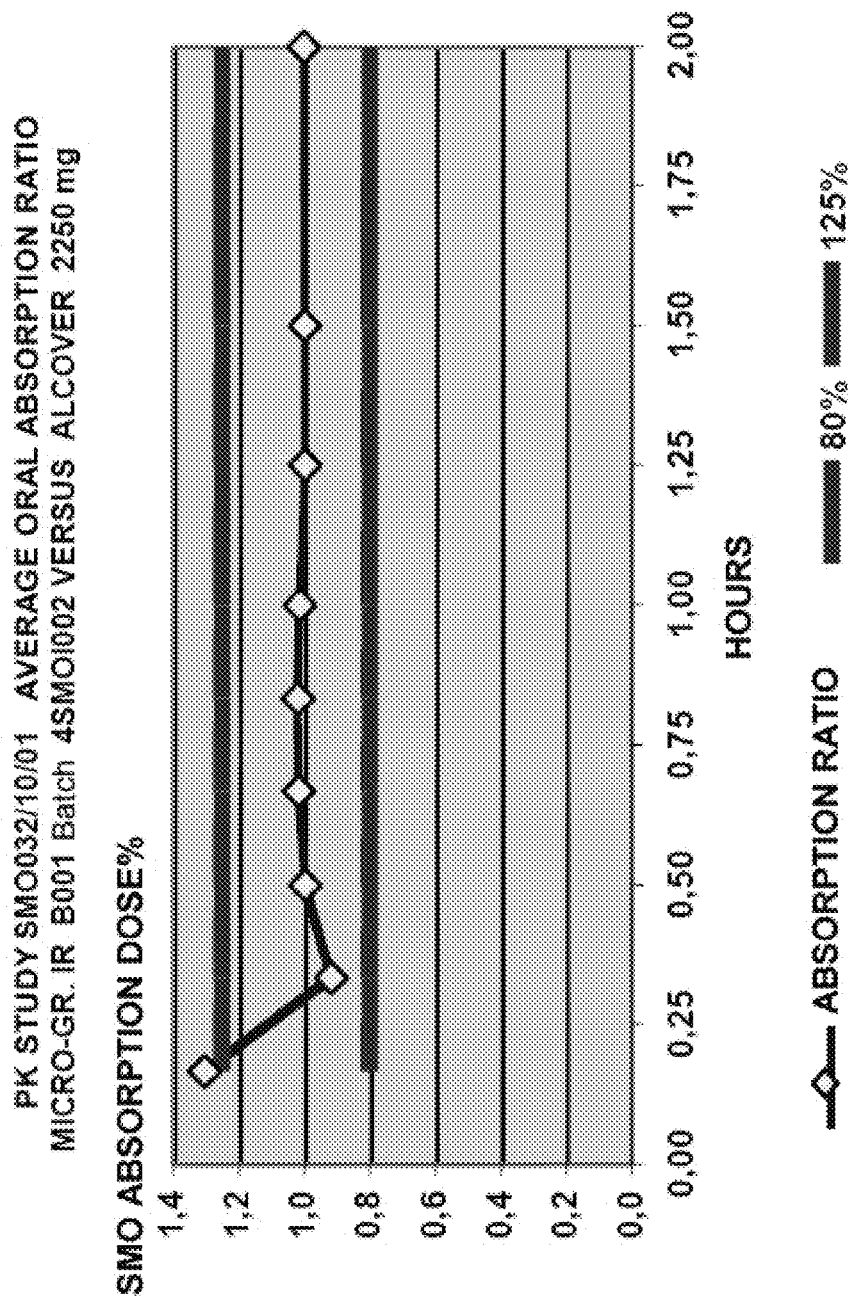
FIG. 14 is a graphic representation of the ratio R data of the absorption profiles of the IR 2,250 mg microgranules (Alcover reference).

Dosage 2,250 mg: Microgranule formulation versus Alcover (the results being illustrated in the following table and FIG. 14):

PK STUDY SMO032/10/01
AVERAGE ORAL ABSORPTION RATIO
MICRO-GR. IR B002 Batch 4SMOI002
VERSUS ALCOVER 2250 mg

| HOURS | MICROG-IR ABSORPTION RATIO |
|---|---|
| 0 | |
| 0.17 | 1.30 |
| 0.33 | 0.91 |
| 0.50 | 1.00 |
| 0.67 | 1.02 |
| 0.83 | 1.02 |
| 1.00 | 1.01 |
| 1.25 | 0.99 |
| 1.50 | 1.00 |
| 2.00 | 1.00 |

The ratio R of the absorption profiles of the IR 2,250 mg microgranules and of the Alcover® solution is included between the values 0.8 and 1.2.

The ratios R of the average cumulative absorption profiles of gamma-hydroxybutric acid of the microgranules and solutions were established at each time between the microgranules and the solutions administered with the same dose: R(t)=dose % (t) after microgranule divided by dose (t) after solution.

The values of these ratios are actually comprised in the 0.8-1.2 interval for the totality of the absorption process (1.0 to 1.23 and 0.96 to 1.0) for the 1,750 mg doses: they are comprised between 1.3 and 0.91 for both dosages of 1,750 and 2,250 mg indicating slightly faster absorption of the microgranules at the very first instants of the kinetics.

Oral absorption of gamma-hydroxybutric acid does not depend on the process for dissolution of the microgranules of batch 4SMOI001 and of batch 4SMOI002.

The results obtained in vivo are perfectly correlated with the results observed in vitro which very clearly indicate extremely fast dissolution (less than 5 minutes) which cannot influence the intestinal absorption of gamma-hydroxybutric acid. The method is therefore perfectly predictive.

V—Study of Instantaneous and Cumulated Dissolution of the Formulations According to the Invention In order to study the in vivo behavior of these formulations, their instantaneous dissolution was evaluated. Thus, the percentage of released active ingredient was assayed at time T, which allows simulation of the in vivo behavior of the composition in the determined fluid.

The cumulated dissolution kinetics will be compared with the change in the plasma level of the active ingredient over time.

The impact of the coating membrane was therefore studied by comparing the differential dissolutions between an immediate form and a coated form.

The sought effect is exclusively here to slow down the diffusion of the active ingredient in the stomach in order to maintain preferential absorption in the upper areas of the digestive tract.

Thus, it is also interesting to have formulations with a dissolution at a release rate of 80% within two hours.

BRIEF DESCRIPTION OF THE DRAWINGS

FIG. 1 is a graphical representation of the results of the study of the instantaneous and cumulated dissolution of the immediate release formulations.

Figure 2:
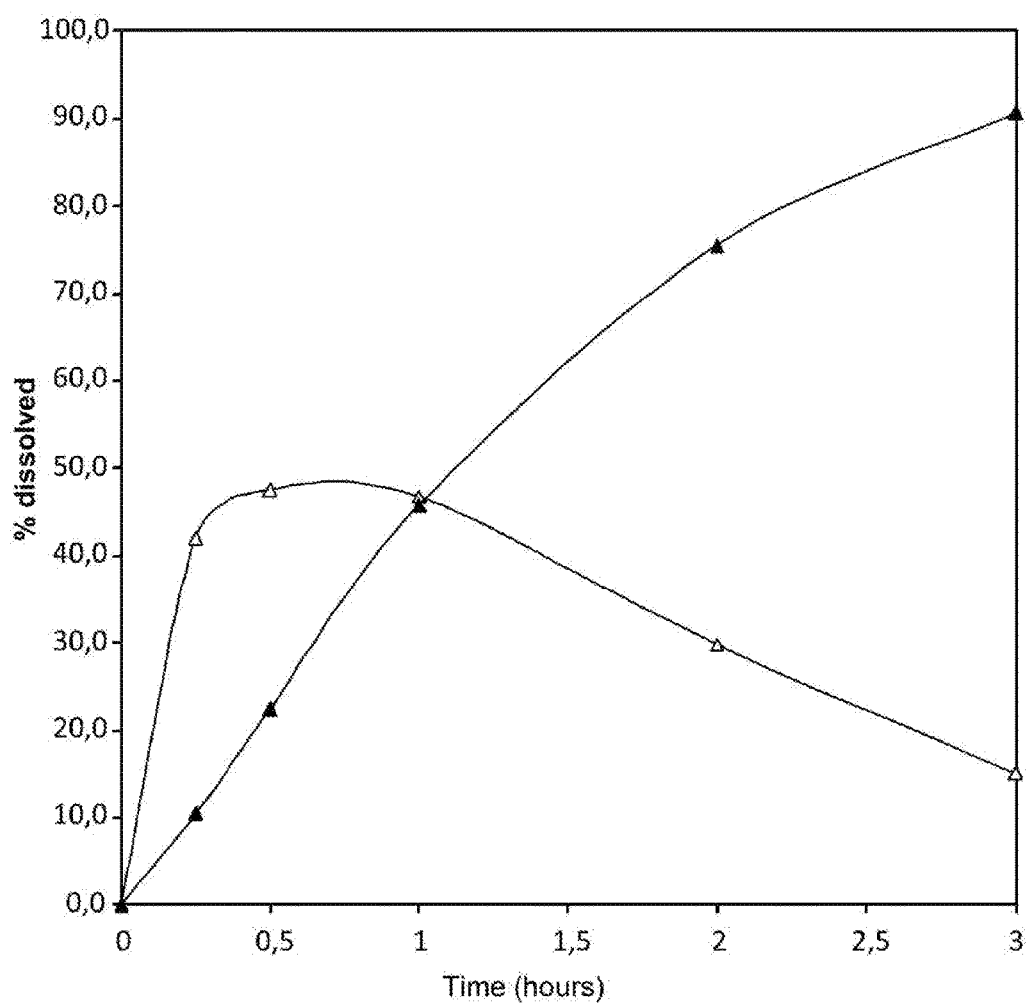
FIG. 2 is a graphic representation of the results of the study of the instantaneous and cumulated dissolution of the delayed release formulations.

FIG. 2 is a graphical representation of the results of the study of the instantaneous and cumulated dissolution of the delayed release formulations.

Figure 3:
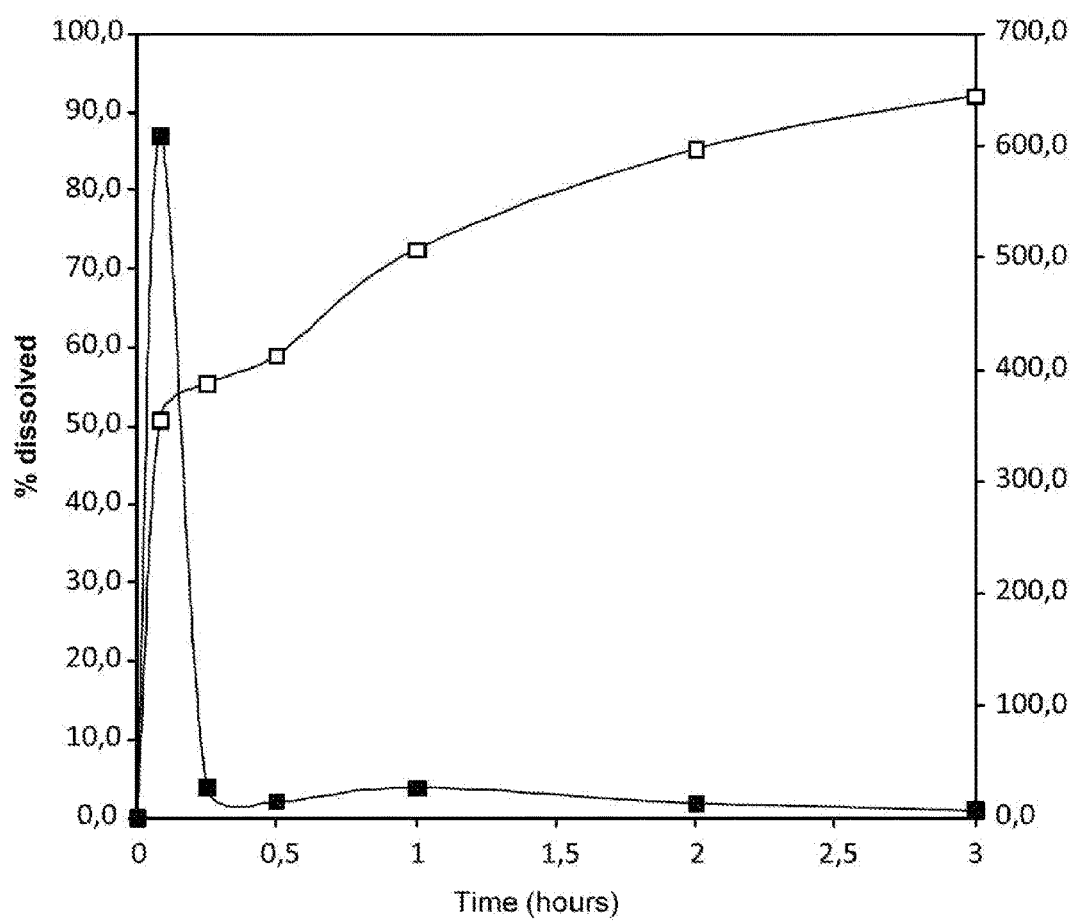
FIG. 3 is a graphic representation of the results of the study of the instantaneous and cumulated dissolution of the mixtures of immediate release and delayed release forms.

FIG. 3 is a graphical representation of the results of the study of the instantaneous and cumulated dissolution of mixtures of immediate release and delayed response forms.

Figure 4:
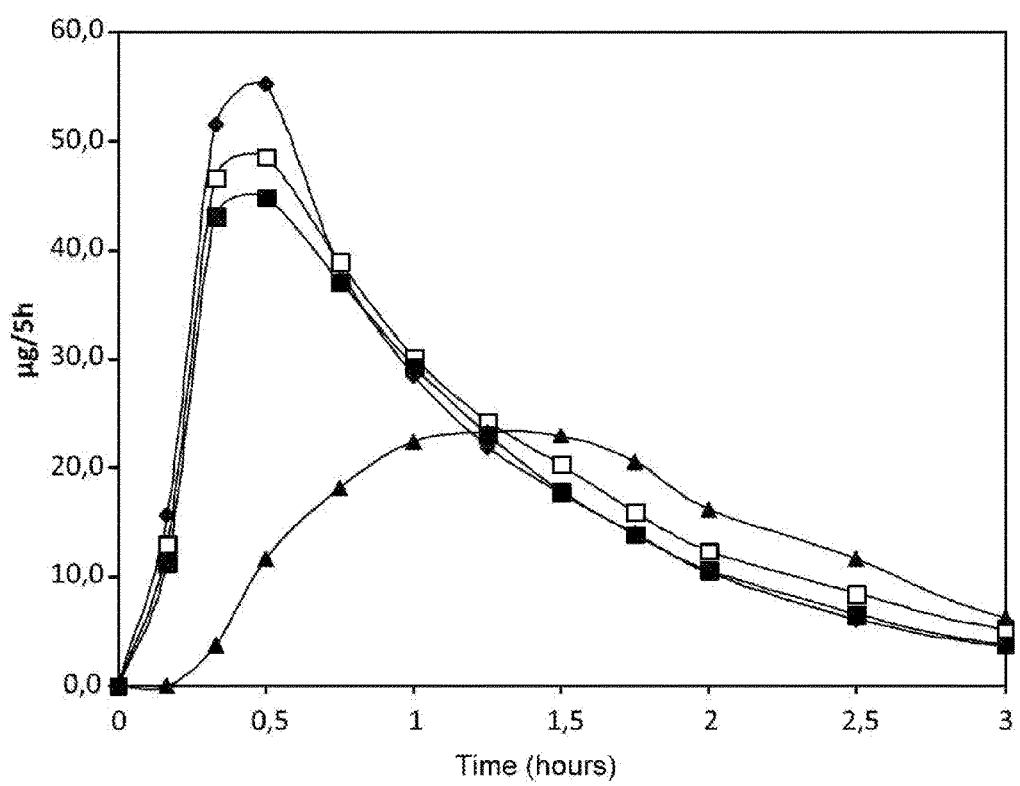
FIG. 4 is a graphic representation of dissolution curves relating to the data obtained from the first human study.

FIG. 4 is a graphical representation of the amount of dissolved active ingredient versus time of Ref. 1 and Ref 2 and Example 1 and Example 2.

Figure 5:
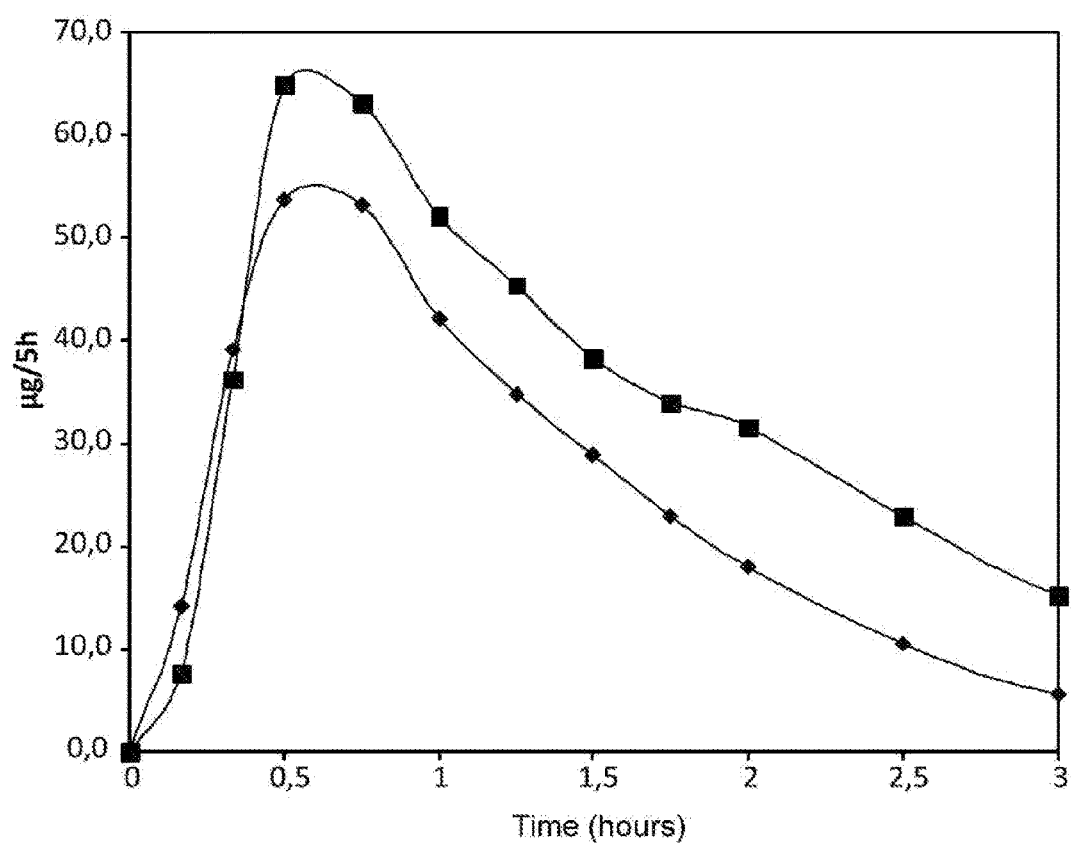
FIG. 5 is a graphic representation of dissolution curves relating to the data obtained from the second human study.

FIG. 5 is a graphical representation of the amount of dissolved active ingredient versus time of Ref. (Xyrem) and Example 3.

The results of the study of the instantaneous and cumulated dissolution of the immediate release formulations are illustrated in FIG. 1. The curve with the black lozenges corresponds to the dissolved percentage of active ingredients (%) versus time (in hours) and the curve with the white lozenges corresponds to the dissolution rate for the formulation of Example 4.

The results of the study of the instantaneous and cumulated dissolution of the delayed release formulations are illustrated in FIG. 2. The curve with the black triangles corresponds to the dissolved percentage of active ingredient (%) versus time (in hours) and the curve with the white triangles corresponds to the dissolution rate for the formulation of Example 5.

The results of the study of the instantaneous and cumulated dissolution of the mixtures of immediate release and delayed release forms are illustrated in FIG. 3. The curve with the black squares corresponds to the dissolved percentage of active ingredients (%) versus time (in hours) and the curve with the black squares corresponds to the dissolution rate for the formulation of Example 3.

VI—Clinical Studies

Two studies were conducted in humans:

1. $1^{st}$ study: formulations SMO.IR and SMO.SR against 2 references (Ref. 1=Alcover®; Ref. 2=Xyrem®), administration of 1.75 g on 12 healthy male volunteers with an empty stomach.

2. $2^{nd}$ study: formulation SMO.MR, administered at 3.0 g against 1 reference Ref.=Xyrem®) administered at 2.25 g on 8 healthy male volunteers with an empty stomach. The parameters extracted from these two studies are reported hereafter.

| Results of the first study | | | | |
|---|---|---|---|---|
| Formula | C max (µg/ml) (average ± SD) | t max (h) (average) | AUC (µg/ml · h) (average ± SD) | $t_{1/2}$ (h) (average ± SD) |
| Ref. 1 (Alcover ®) | 50.19 ± 15.27 | 0.50 | 61 ± 31 | 0.55 ± 0.14 |
| Ref. 2 (Xyrem ®) | 55.37 ± 16.45 | 0.50 | 64 ± 31 | 0.57 ± 0.21 |
| SMO.IR (Example 1) | 54.47 ± 15.75 | 0.50 | 70 ± 46 | 0.56 ± 0.26 |
| SMO.SR (Example 2) | 31.35 ± 20.67 | 1.25 | 52 ± 39 | 0.56 ± 0.26 |

| Results of the second study | | | | |
|---|---|---|---|---|
| Formula | C max (µg/ml) (average ± SD) | t max (h) (average) | AUC (µg/ml · h) (average ± SD) | $t_{1/2}$ (h) (average ± SD) |
| Ref. (Xyrem ®) | 61.95 ± 14.21 | 0.50 | 83 ± 30 | 0.53 ± 0.11 |
| SMO.MR (Example 3) | 68.52 ± 12.13 | 0.50 | 121 ± 54 | 0.62 ± 0.22 |

The dissolution curves of both of these studies are respectively illustrated in FIGS. 4 and 5. These figures represent the amounts of dissolved active ingredient (in µg/h) versus time (h).

In FIG. 4, the curve with the black squares corresponds to Ref. 1, the curve with the black lozenges corresponds to Ref. 2, the curve with the white squares corresponds to the formulation of Example 1 and the curve with the black triangles corresponds to the formulation of Example 2.

In FIG. 5, the curve with the black lozenges corresponds to the Ref. (Xyrem) and the curve with the black squares corresponds to the formulation of Example 3.

The tested solid immediate formulation has pharmacokinetic parameters equivalent to those of two tested liquid oral forms; a bioequivalence is obtained between the tested formulation and Reference 1.

It is also noted for the immediate formulations that the ascending portions (absorption) and descending portions (elimination) are equivalent which suggests a linear phenomenon.

The invention claimed is:

1. A coated granule composed of a solid core on which is supported
    an active ingredient, the active ingredient being selected from gamma hydroxybutric acid or one of its pharmaceutically acceptable salts,
    a gas generator,
    a diluent,
    a binder, and
    a coating membrane, where
        the coating membrane is a layer surrounding the active ingredient, the gas generator, the diluent, and the binder, and the layer has a surface that is an outermost surface of the coated granule; wherein
        the coated granule consists of the following, by weight based on the total weight of the granule:
        15-25% of the solid core,
        50-60% of the active ingredient,
        5-15% of the gas generator,
        2-18% of the diluent,
        3-10% of the binder,
        3-6% of the coating membrane;
        the gas generator is sodium bicarbonate;
        the diluent is magnesium aluminometasilicate; and
        the binder is shellac.

2. The granule according to claim 1, wherein the solid core is one or more member selected from the group consisting of polyols, gums, derivatives of silica, calcium derivatives, potassium derivatives, mineral compounds, dicalcium phosphates, tricalcium phosphates, calcium carbonates, saccharose, cellulose derivatives, microcrystalline cellulose, ethyl cellulose, hydroxypropylmethylcellulose, and starch.

3. The granule according to claim 1, wherein the coating membrane consists of coating excipients for immediate release.

4. The granule according to claim 1, wherein the coating membrane consists of coating excipients for sustained release.

5. The granule according to claim 1, wherein
    the magnesium aluminometasilicate is synthetic and amorphous.

6. A pharmaceutical composition comprising a mixture of granules including the coated granule according to claim 1, wherein said mixture consists of two groups of granules having different kinetics for releasing the active ingredient.

7. A method for treating a pathology requiring at least very fast in vivo availability of GHB, the method comprising administering an effective amount of a composition comprising the coated granule of claim 1 to a patient to treat the pathology.

8. The method according to claim 7, wherein the pathology is narcolepsy.

9. The method according to claim 7, wherein the pathology is alcoholic withdrawal.

10. A pharmaceutical composition comprising:
    at least one coated granule according to claim 1, and
    granules of a sweetener.

* * * * *